(12) United States Patent
Fuller et al.

(10) Patent No.: US 8,088,214 B2
(45) Date of Patent: Jan. 3, 2012

(54) TRANSPARENT GONIOCHROMATIC MULTILAYER EFFECT PIGMENT

(75) Inventors: Daniel S. Fuller, Beacon, NY (US); Curtis J. Zimmermann, Cold Spring, NY (US)

(73) Assignee: BASF Corporation, Florham Park, NJ (US)

( * ) Notice: Subject to any disclaimer, the term of this patent is extended or adjusted under 35 U.S.C. 154(b) by 544 days.

(21) Appl. No.: 11/351,416

(22) Filed: Feb. 10, 2006

(65) Prior Publication Data

US 2006/0180049 A1 Aug. 17, 2006

Related U.S. Application Data

(60) Provisional application No. 60/652,020, filed on Feb. 12, 2005.

(51) Int. Cl.
- *C09C 1/36* (2006.01)
- *C09C 1/00* (2006.01)
- *C04B 14/04* (2006.01)

(52) U.S. Cl. .......................... 106/436; 106/481; 106/415

(58) Field of Classification Search .................. 106/400, 106/415

See application file for complete search history.

(56) References Cited

U.S. PATENT DOCUMENTS

| | | | | |
|---|---|---|---|---|
| 3,627,553 A | | 12/1971 | Clark et al. .................... | 106/300 |
| 4,434,010 A | | 2/1984 | Ash .............................. | 106/291 |
| 5,456,749 A | | 10/1995 | Iwasa et al. .................... | 106/417 |
| 6,132,873 A | | 10/2000 | Dietz et al. .................... | 428/404 |
| 6,280,520 B1 | | 8/2001 | Andes et al. ................... | 106/415 |
| 6,451,294 B1 | | 9/2002 | Simon | |
| 6,500,251 B1 | * | 12/2002 | Andes et al. ................... | 106/415 |
| 6,517,628 B1 | | 2/2003 | Pfaff et al. .................... | 106/417 |
| 6,524,381 B1 | * | 2/2003 | Phillips et al. ................. | 106/417 |
| 6,533,857 B1 | * | 3/2003 | Schmid et al. ................. | 106/403 |
| 6,565,770 B1 | * | 5/2003 | Mayer et al. .............. | 252/301.36 |
| 6,569,529 B1 | * | 5/2003 | Phillips et al. ................. | 428/403 |
| 6,596,070 B1 | * | 7/2003 | Schmidt et al. ................ | 106/417 |
| 6,620,233 B1 | * | 9/2003 | Seeger et al. .................. | 106/417 |
| 6,632,275 B1 | * | 10/2003 | Schoen et al. ................. | 106/404 |
| 6,656,259 B2 | | 12/2003 | Pfaff et al. ..................... | 106/415 |
| 6,663,852 B2 | | 12/2003 | Simon | |
| 6,676,741 B2 | * | 1/2004 | Phillips et al. ................. | 106/417 |
| 6,686,042 B1 | * | 2/2004 | LeGallee ....................... | 428/403 |
| 6,689,205 B1 | | 2/2004 | Bruckner et al. .............. | 106/415 |
| 6,719,838 B2 | | 4/2004 | Heider et al. .................. | 106/417 |
| 2002/0104461 A1 | | 8/2002 | Schmidt et al. ................ | 106/417 |
| 2003/0039836 A1 | | 2/2003 | Pfaff ............................. | 428/404 |
| 2003/0092815 A1 | | 5/2003 | Steudel ......................... | 524/442 |
| 2004/0000692 A1 | | 1/2004 | Yamashita et al. | |
| 2004/0003758 A1 | | 1/2004 | Bruckner et al. .............. | 106/415 |
| 2004/0052743 A1 | | 3/2004 | Schmidt et al. .................. | 426/63 |
| 2004/0134385 A1 | | 7/2004 | Anselmann et al. .......... | 106/415 |
| 2004/0139889 A1 | | 7/2004 | Zimmermann | |
| 2004/0170838 A1 | | 9/2004 | Ambrosius et al. ........... | 428/406 |

FOREIGN PATENT DOCUMENTS

| | | |
|---|---|---|
| CA | 2238035 | 3/1998 |
| JP | 7-246366 | 9/1995 |
| WO | WO 98/53011 | 11/1998 |
| WO | WO 02/090448 A2 | 11/2002 |
| WO | WO 03/006558 A2 | 1/2003 |

\* cited by examiner

*Primary Examiner* — Shuangyi Abu Ali
(74) *Attorney, Agent, or Firm* — Bernard Lau

(57) ABSTRACT

A multilayer effect pigment includes a transparent substrate, a layer of high refractive index material on the substrate, and alternating layers of low refractive index and high refractive index materials on the first layer, the total number of layers being an odd number of at least three, all adjacent layers differing in refractive index by at least about 0.2 and at least one of the layers having an optical thickness which is different from all of the other layers. The resulting multilayer effect pigment is not a quarter-wave stack. The present effect pigments may be used in cosmetic and industrial applications.

21 Claims, No Drawings

TRANSPARENT GONIOCHROMATIC MULTILAYER EFFECT PIGMENT

This application claims priority to U.S. Provisional Application Ser. No. 60/652,020, filed Feb. 12, 2005.

BACKGROUND OF THE INVENTION

Effect pigments, also known as pearlescent or nacreous pigments, are based on the use of a laminar substrate such as mica or glass flake which has been coated with a metal oxide layer. These pigments exhibit pearl-like luster as a result of reflection and refraction of light, and depending on the thickness of the metal oxide layer, they can also exhibit interference color effects.

Titanium dioxide-coated mica and iron oxide-coated mica effect pigments are the effect pigments which are encountered most often on a commercial basis. Pigments in which the metal oxide has been over-coated with another material are also well known in the art.

The commercially available effect pigments which contain only a single coating of a high refractive index material provide only two reflecting interfaces between materials. These two material interfaces (and reflections) are therefore solely responsible for the reflectivity achieved from the platelet surface. A substantial percentage of the incident light is thus transmitted through the platelet and while this is necessary to create the nacreous appearance of the pigment, it also diminishes other desirable properties of the effect pigments such as luster, chromaticity and hiding power. To counteract this consequence, the art has either mixed the effect pigments with other pigments or added additional layers of transparent and/or selectively absorbing materials onto the effect pigment.

Examples of prior art describing multi-coated effect pigments include JP 7-246366, WO 98/53011, WO 98/53012 and U.S. Pat. No. 4,434,010. All of such prior art requires that each coated layer possess an optical thickness equal to a whole number multiple of a one-quarter of the wavelength at which interference is expected. Such construction of the so-called quarter-wave stacks is a widely accepted and implemented condition in the thin-film industries. Because of this limitation, a unique layer thickness combination is essential in order to create each individual one of the interference colors of the visible spectrum. The base substrate is the only dimension common to all of the compositions displaying different interference colors.

It has now been discovered that the adherence to the quarter-wave stack approach is unnecessary and suitable products, even with substantial gains in luster, chromaticity and hiding power, can be achieved without observing that requirement. Further, numerous other advantages can be realized.

It is accordingly the object of this invention to provide a new multilayer effect pigment, including having improved luster, chromaticity and/or hiding power relative to other effect pigments.

SUMMARY OF THE INVENTION

This invention relates to a multilayer effect pigment and more particularly, to a multilayer effect pigment which includes a transparent substrate having a transparent high refractive index material layer thereon and at least one pair of layers which are a transparent high refractive index material and a transparent low refractive index material, in which the total number of layers is an odd number, in which every two adjacent non-substrate layers differ in refractive index by at least about 0.2 and in which at least one layer has an optical thickness which is different from all of the other layers, whereby the pigment is not a quarter-wave stack.

Thus, the present invention provides a multilayer effect pigment comprising: a transparent substrate having a first layer of titanium dioxide thereon, the optical thickness of the first layer of titanium dioxide being such as to provide a white hue to the substrate;

a second layer of a low refractive index material on the first layer and an outermost layer of a high refractive index material placed on the second layer;

the outermost layer comprising titanium dioxide having a optical thickness of from about 45 to 240 nm, the second layer of low refractive index material having a optical thickness of at least 150 nm to provide a variable pathlength for light dependent on the angle of incidence of light impinging thereon;

each layer differs in refractive index from any adjacent layer by at least about 0.2 and wherein at least one layer has an optical thickness which is different from all of the other layers, whereby the pigment is not a quarter-wave stack; and the multilayer effect pigment having a non-white hue.

DESCRIPTION OF THE INVENTION

In accordance with the present invention, the effect pigment is a multilayered product composed of a transparent substrate having an odd number of layers thereon and in which at least one of the layers has an optical thickness which is different from all of the other layers causing the pigment not to be a quarter-wave stack.

Any encapsulatable smooth and transparent platelet can be used as the substrate in the present invention. Examples of useable platelets include mica, whether natural or synthetic, kaolin, glass flakes, bismuth oxychloride, platy aluminum oxide, or any transparent platelet of the proper dimensions. The substrate need not be totally transparent but should, preferably, have at least about 75% transmission. The size of the platelet shaped substrate is not critical per se and can be adapted to the particular use. Generally, the particles have major dimensions averaging about 5-250 microns, preferably 5-100 microns, and an aspect ratio greater than about 5. The specific free surface area (BET) of the substrate is, in general, from about 0.2 to 25 m$^2$/g.

The layers encapsulating the substrate alternate between high refractive index materials and low refractive index materials. High refractive index materials include those with a refractive index from about 2.00 to about 3.10. Low refractive index materials include those with a refractive index from about 1.30 to about 1.80. The high refractive index materials may be anatase titanium dioxide, rutile titanium dioxide, iron oxide, zirconium dioxide, zinc oxide, zinc sulfide, bismuth oxychloride or the like.

The CRC Handbook of Chemistry and Physics, 63$^{rd}$ edition reports refractive indices for these high refractive index materials as follows.

| Material | Refractive Index |
| --- | --- |
| TiO2 - anatase | 2.55 |
| TiO2 - rutile | 2.90 |
| Fe2O3 - hematite | 3.01 |
| ZrO2 | 2.20 |
| ZnO | 2.03 |
| ZnS | 2.38 |
| BiOCl | 2.15 |

The low refractive index material may be silicon dioxide, magnesium fluoride, aluminum oxide, a polymer such as polymethyl methacrylate, polystyrene, ethylene vinyl acetate, polyurea, polyurethane, polydivinyl benzene and the like.

The CRC Handbook of Chemistry and Physics, 63$^{rd}$ edition reports refractive indices for these low refractive index materials as follows.

| Material | Refractive Index |
|---|---|
| SiO2 - amorphous | 1.46 |
| MgF2 | 1.39 |
| Al2O3 | 1.76 |
| Polymers | 1.4-1.6 is typical |

Any combination of materials may be selected provided that adjacent layers differ in refractive index by at least about 0.2, and more preferably at least about 0.6. The materials are transparent but may, like iron oxide, have an absorption component.

The phrase "a transparent substrate having a layer of titanium dioxide thereon" as used herein means that the titanium dioxide may be in direct contact with the transparent substrate or additives or other layers may be present between the transparent substrate and the layer of titanium dioxide. The phrase "a layer of a low refractive index material on said titanium dioxide layer" as used herein means that the low refractive index material layer may be in direct contact with the titanium dioxide layer or additives or other layers may be present between the low refractive index material layer and the titanium dioxide layer. The phrase "outermost titanium dioxide layer on said low refractive index material layer" as used herein means that the outermost titanium dioxide layer may be in direct contact with said low refractive index material layer or additives or other layers may be present between the low refractive index material layer and the outermost titanium dioxide layer.

The individual layers can be applied to the substrate and to each other using techniques well known in the art. Any such technique can be utilized. One of the advantages of the invention is that sol-gel techniques can be used to apply the coatings. Such techniques are well known and widely practiced for thin film deposition, and are safe, economical and amenable to a wide variety of particle shapes and sizes. Chemical vapor deposition techniques which have been used in some prior art have a litany of negative aspects including safety hazards, expensive reagents and infrastructure and substrate particle size limitations. Monolithic web-based multilayer coating techniques have also been used in the prior art and suffer from the disadvantages that pigment particles are formed after the coatings are applied and therefore have discontinuities in the layers at the fracture points. The particles must also be classified according to size after the monolith is fractured, whereas in the present invention the particle size can be predetermined before the coating and can be constant. Useful additives include rutile directors for titanium dioxide such as tin.

Another advantage of the present invention is that the substrate and all layers have an appreciable degree of transparency and therefore the resulting pigments can exhibit unique angle dependent reflectivity ranging from nearly totally reflecting to substantially transmitting as the viewing angle is changed. Many multi-coated pigments in the prior art use metal flakes as substrates and such metal layers are not capable of transmitting light and the resulting pigment is therefore totally opaque.

Because the pigment is not a quarter-wave stack, the first layer which is adjacent the substrate can be given a fixed optical thickness and by varying the thickness of the other layers, it is possible to prepare all of the interference colors desired. Further, the first and second coating layers may be fixed and such coated substrates may be used to prepare multiple final products by variation of the final layer only. The number of unique layer combinations necessary to prepare all of the interference colors with the present invention is much less than for the prior art. The adherence to the quarter-wave optical thickness condition for the layers of the prior art compositions precludes the use of universal single or double coated precursors to three layer compositions.

While any odd number of layers equal to or greater than three can be employed, it has been found that substantial advantages are present when there are three layers and this is therefore preferred.

As described below, the thicknesses of each of the individual layers applied to the substrate are described as the optical thickness values. Optical thickness is the product of the actual physical or geometric thickness (t) of the layer and the refractive index (n) of the material of the layer. While it may be possible to measure the physical thickness of the deposited layer on the substrate, the refractive index of the applied material will vary from published values depending on the density and uniformity of the deposited layer. Typically, the tabulated values of refractive index are well known but such values are determined from a uniform and highly packed structure and are almost always higher than the refractive index values of the actual layers deposited via the techniques of this invention. Accordingly, it may be difficult to obtain the desired color by simply applying the respective materials at a prescribed physical thickness of the layer in as much as the refractive index may vary widely depending on the density and uniformity of the coating. However, the optical thickness can be indirectly determined by measuring the wavelengths at which interferences occur in the sample and then solving for "nt" in the well-known constructive interference and/or destructive interference equations. The equations as written below are for normal angle incidence of light only, in which the cosine θ term reduces to 1 and does not need to appear, in the interest of simplifying the present discussion.

Constructive interference equation: $nt = m\lambda/4$ where in m=odd integer
n=refractive index of the film material
t=geometric (physical) thickness of the film material, in nanometers
λ=the wavelength of maximum reflection, in nanometers
nt=optical thickness of the film material, in nanometers
Destructive interference equation: $nt = m\lambda/2$ where in m=any positive integer
λ=the wavelength of minimum reflection, in nanometers By measuring the interference wavelength λ from samples having the desired color after each layer deposition, the optical thickness of each layer can be readily determined. It is important to note that in this invention, the optical thicknesses of all the layers are not the same and as such, the pigment of the present invention does not represent the typical quarter wave stack. A layer having the appropriate whole integer multiple for the coefficient "m" in the equations is considered to possess the same optical thickness as the m=1 case, and therefore construction of a stack of layers in which the integer m is varied at a constant λ is still considered a quarter-wave stack based on its function. This practice is therefore avoided in this invention. Surprisingly, it has been found that non-quarter wave stack pigments can yield desired colors contrary to what was long considered in the art, that the optical thicknesses of all the layers had to be the same.

The low refractive index material is preferably silica and while this can have other thicknesses, the silica layer preferably has a optical thickness of at least 150 nm, preferably in the range of about 180-730 nm, and more preferably about 215-470 nm. This maximizes the degree of angle dependent color travel, which is inherent in silica films. In this invention, the silica layers will have a optical thickness to provide a variable pathlength for light dependent on the angle of incidence of light impinging thereon. It is preferred that the low refractive index material layer have a sufficient thickness to provide greater than 75 and, more preferably, more than 100 degrees of hue angle color travel.

The first layer on the substrate and the outermost layer can be the same or different, and are further preferably titanium dioxide. It will be appreciated that where the first or innermost layer has a fixed optical thickness and the low refractive index layer also has a predetermined optical thickness, the outermost high refractive index layer will control the interference color as a result of its optical thickness. The substrate/first layer/second layer combination thus acts as a universal base from which all interference colors can be realized by simply varying the optical thickness of the third layer. In general, it is useful to provide a first layer of titanium dioxide on the substrate, which will lead to a preliminary white-colored material. As such, the optical thickness of the first titanium dioxide layer will generally range from about 105 to 155 nm.

The optical thickness of the third layer, when it is titania, in such an arrangement generally varies from about 45 to 240 nm, and preferably about 95-240 nm. More consistent color can be achieved if the outermost titania layer has an optical thickness of at least 95 nm. The pigments of this invention have non-white hues. A "non-white" hue according to this invention means the pigments of this invention will have a chromaticity (0° C.*) of at least 40.0 and are not a white to pearl or silvery color.

The phrase "grazing angle" as used herein means a viewing angle that is almost parallel to the sample surface. This is in contrast to the phrase "face angle" which means a viewing angle that is almost perpendicular to the sample surface.

The products of the present invention can be used in any application where pearlescent pigments have been used heretofore. Thus, the products of this invention have an unlimited use in all types of automotive and industrial paint applications, especially in the organic color coating and inks field where deep color intensity is required. For example, these pigments can be used in mass tone or as styling agents to spray paint all types of automotive and non-automotive vehicles. Similarly, they can be used on all clay/formica/wood/glass/metal/enamel/ceramic and non-porous or porous surfaces. The pigments can be used in powder coating compositions. They can be incorporated into plastic articles geared for the toy industry or the home. These pigments can be impregnated into fibers to impart new and esthetic coloring to clothes and carpeting. They can be used to improve the look of shoes, rubber and vinyl/marble flooring, vinyl siding, and all other vinyl products. In addition, these colors can be used in all types of modeling hobbies.

The above-mentioned compositions in which the compositions of this invention are useful are well known to those of ordinary skill in the art. Examples include printing inks, nail enamels, lacquers, thermoplastic and thermosetting materials, natural resins and synthetic resins. Some non-limiting examples include polystyrene and its mixed polymers, polyolefins, in particular, polyethylene and polypropylene, polyacrylic compounds, polyvinyl compounds, for example polyvinyl chloride and polyvinyl acetate, polyesters and rubber, and also filaments made of viscose and cellulose ethers, cellulose esters, polyamides, polyurethanes, polyesters, for example polyglycol terephthalates, and polyacrylonitrile.

For a well-rounded introduction to a variety of pigment applications, see Temple C. Patton, editor, The Pigment Handbook, volume II, Applications and Markets, John Wiley and Sons, New York (1973). In addition, see for example, with regard to ink: R. H. Leach, editor, The Printing Ink Manual, Fourth Edition, Van Nostrand Reinhold (International) Co. Ltd., London (1988), particularly pages 282-591; with regard to paints: C. H. Hare, Protective Coatings, Technology Publishing Co., Pittsburgh (1994), particularly pages 63-288. The foregoing references are hereby incorporated by reference herein for their teachings of ink, paint and plastic compositions, formulations and vehicles in which the compositions of this invention may be used including amounts of colorants. For example, the pigment may be used at a level of 10 to 15% in an offset lithographic ink, with the remainder being a vehicle containing gelled and ungelled hydrocarbon resins, alkyd resins, wax compounds and aliphatic solvent. The pigment may also be used, for example, at a level of 1 to 10% in an automotive paint formulation along with other pigments which may include titanium dioxide, acrylic lattices, coalescing agents, water or solvents. The pigment may also be used, for example, at a level of 20 to 30% in a plastic color concentrate in polyethylene.

In the cosmetic and personal care field, these pigments can be used in the eye area and in all external and rinse-off applications. They are restricted only for the lip area. Thus, they can be used in hair sprays, face powder, leg-makeup, insect repellent lotion, mascara cake/cream, nail enamel, nail enamel remover, perfume lotion, and shampoos of all types (gel or liquid). In addition, they can be used in shaving cream (concentrate for aerosol, brushless, lathering), skin glosser stick, skin makeup, hair groom, eye shadow (liquid, pomade, powder, stick, pressed or cream), eye liner, cologne stick, cologne, cologne emollient, bubble bath, body lotion (moisturizing, cleansing, analgesic, astringent), after shave lotion, after bath milk and sunscreen lotion.

The present effect pigments may also be used in combination with food or beverages or to coat foods.

In order to further illustrate the invention, various examples are set forth below. In these examples, as well as throughout this specification and claims, all parts and percentages are by weight and all temperatures are in degrees Centigrade, unless otherwise indicated.

EXAMPLE 1

A 5 liter Morton flask was equipped with a mechanical stirrer and charged with a suspension of 150 grams of mica of average diameter 50 microns in 1.0 liter of $H_2O$. The slurry was heated to 74° C. and stirred at 200 RPM and lowered to pH 2.2 with HCl. A 40% $TiCl_4$ solution was pumped in at 0.75 mls. per minute at pH 2.2 until the mica shade was a white pearl, requiring 190 grams of solution. The pH was kept constant by adding 35% NaOH solution during the addition.

The slurry pH was raised rapidly to 8.25 by adding 35% NaOH solution, and the stirring rate was raised to 250 RPM. 1563.0 grams of 20% $Na_2SiO_3 \cdot 5H_2O$ solution were added at 5.7 grams/minute while maintaining the pH at 8.25 with 28% HCl solution. A small sample of suspension was then filtered and calcined at 850° C. The interference color of the platelet was yellow as predicted from the titania plus silica film combination.

The suspension pH was then lowered to 2.2 by adding 28% HCl solution at a rate of 0.75 mls/minute. The stirring rate was lowered again to 200 RPM. The second titania layer was coated by again adding 40% $TiCl_4$ solution at 0.75 mls/minute. A few small samples of suspension were filtered, calcined at 850° C., and evaluated in drawdown until the target product was obtained at 253 grams of added 40% $TiCl_4$. The entire suspension was then processed to yield the desired calcined product which exhibited a high chromaticity green normal color which flopped to a violet color at a grazing angle of the drawdown card. The color properties of the pigment agreed with the properties of Sample 19 in the Table of Example 6.

EXAMPLE 2

A 5 liter Morton flask was equipped with a mechanical stirrer and charged with a suspension of 832 grams of borosilicate glass flake of average diameter 100 microns in 1.67 liters of $H_2O$. The suspension was heated to 80° C., stirred at 300 RPM and adjusted to pH 1.4 with 28% HCl. 47.0 grams of 20% $SnCl_4.5H_2O$ solution were pumped in at 2.4 grams per minute while maintaining the pH at 1.4 with 35% NaOH solution, and then the suspension was stirred for a 30 minute digestion period at temperature.

A 40% $TiCl_4$ solution was added at 2.0 grams per minute until a white pearl shade was imparted to the glass at 144 grams of added solution. No sample was withdrawn, and the suspension pH was rapidly raised to 8.25 by adding 35% NaOH solution, which was also used to control the pH at 1.4 during the $TiCl_4$ addition. The temperature was lowered to 74° C., and then 1290.0 grams of 20% $Na_2SiO_3.5H_2O$ solution were added at 5.4 grams per minute while controlling the pH at 8.25 with 28% HCl solution. A small sample of the suspension was filtered and calcined at 625° C.

The suspension pH was lowered to 1.4 with 28% HCl solution added at 0.8 mls/minute, and the temperature was returned to 80° C. The previous $SnCl_4.5H_2O$ addition step was repeated verbatim, as was the 40% $TiCl_4$ addition. Three samples of the suspension were filtered and calcined at 625° C. after 106 grams, 164 grams and 254 grams of added $TiCl_4$ solution respectively. The normal interference colors of the 3 samples were blue, turquoise and green which flopped to red, violet and blue-violet respectively at grazing viewing angles. The green normal color sample was essentially an exact analog to the final product yielded in Example 1. All three samples exhibited substantially higher chromaticity than the commercially available singly coated glass flake products (Engelhard Corporation REFLECKS™). The blue pigment had color properties which agreed with Sample 8 of the Table in Example 6.

EXAMPLE 3

Following the general procedure given in Example 2, a red to yellow color shifting effect pigment was prepared by repeating the first TiO2 layer white pearl shade of Example 1, adding 860.3 grams of the 20% $Na_2SiO_3.5H_2O$ solution, and a final $TiO_2$ layer from 293 grams of 40% $TiCl_4$ solution. The pigment had color properties which agreed with Sample 3 of the Table of Example 6.

EXAMPLE 4

Following the general procedure given in Example 2, a violet to orange color shifting effect pigment was prepared by repeating the first $TiO_2$ layer white pearl shade, adding 1147.0 grams of the 20% $Na_2SiO_3.5H_2O$ solution, and a final $TiO_2$ layer from 133 grams of added 40% $TiCl_4$ solution. The pigment had color properties which agreed with Sample 5 of the Table of Example 6.

EXAMPLE 5

A 5 liter Morton flask was equipped with a mechanical stirrer and charged with a suspension of 250 grams of borosilicate glass flake of average diameter 81 microns and a BET specific surface area measured at 0.75 $m^2/gr.$ in 1.2 liters of $H_2O$. The suspension was heated to 82° C., stirred at 300 RPM and adjusted to pH 1.4 with 28% HCl. 56.0 grams of 20% $SnCl_4.5H_2O$ solution were pumped in at 2.4 grams per minute while maintaining the pH at 1.4 with 35% NaOH solution, and then the suspension was stirred for a 30 minute digestion period at temperature.

A 40% $TiCl_4$ solution was added at 2.0 grams per minute until a white pearl shade was imparted to the glass at 173 grams of added solution. No sample was withdrawn, and the suspension pH was rapidly raised to 8.25 by adding 35% NaOH solution, which was also used to control the pH at 1.4 during the $TiCl_4$ addition. The temperature was lowered to 74° C., and then 1393.8 grams of 20% $Na_2SiO_3.5H_2O$ solution were added at 5.4 grams per minute while controlling the pH at 8.25 with 28% HCl solution. A small sample of the suspension was filtered and calcined at 625° C. and the dry interference color was the same as that of the titania plus silica combination in example 1.

The suspension pH was lowered to 1.4 with 28% HCl solution added at 1.0 mls/minute, and the temperature was returned to 82° C. The previous $SnCl_4.5H_2O$ addition step was repeated verbatim, as was the 40% $TiCl_4$ addition. Three samples of the suspension were filtered and calcined at 625° C. after 133 grams, 190 grams and 281 grams of added $TiCl_4$ solution respectively. The normal interference colors of the 3 samples were blue, turquoise and green which flopped to red, violet and blue-violet respectively at grazing viewing angles. The 3 samples were essentially exact analogs to the products yielded in Example 2.

EXAMPLE 6

Effect pigment products are set forth in the following table.

| | | Film Optical Thickness and Theoretical Color Data | | | | | | | | | | |
|---|---|---|---|---|---|---|---|---|---|---|---|---|
| Sample No. | Normal Color[3] | First $TiO_2$ Layer, $Nm^1$ | Silica Layer, $Nm^2$ | Second $TiO_2$ Layer, $Nm^1$ | 0° L* | 0° a* | 0° b* | 0° C* | 60° L* | 60° a* | 60° b* | 60° C* |
| 1 | Gold | 134 | 219 | 95 | 85.7 | −10.6 | 54.5 | 55.5 | 85.7 | −6.7 | 7.7 | 10.2 |
| 2 | Gold | 134 | 263 | 48 | 76.3 | 0.8 | 53.2 | 53.2 | 80.5 | −8.1 | 13.9 | 16.1 |
| 3 | Red | 134 | 219 | 177 | 71.0 | 43.5 | −0.6 | 43.5 | 84.3 | −12.8 | 49.7 | 51.3 |
| 4 | Red | 134 | 467 | 215 | 70.9 | 42.5 | 0.3 | 42.5 | 82.0 | −21.0 | 32.0 | 38.3 |

-continued

Film Optical Thickness and Theoretical Color Data

| Sample No. | Normal Color[3] | First TiO$_2$ Layer, Nm[1] | Silica Layer, Nm[2] | Second TiO$_2$ Layer, Nm[1] | 0° L* | 0° a* | 0° b* | 0° C* | 60° L* | 60° a* | 60° b* | 60° C* |
|---|---|---|---|---|---|---|---|---|---|---|---|---|
| 5 | Violet | 134 | 292 | 95 | 59.1 | 60.8 | −48.9 | 78.0 | 78.9 | −1.2 | 33.0 | 33.0 |
| 6 | Violet | 134 | 307 | 72 | 55.1 | 66.3 | −52.8 | 84.8 | 77.0 | −1.4 | 35.6 | 35.6 |
| 7 | Violet | 134 | 329 | 48 | 51.5 | 63.8 | −54.5 | 83.9 | 73.8 | −0.8 | 36.9 | 36.9 |
| 8 | Blue | 134 | 329 | 95 | 62.2 | 0.1 | −51.0 | 51.0 | 71.2 | 27.8 | −4.7 | 28.2 |
| 9 | Blue | 134 | 336 | 84 | 60.4 | 1.7 | −53.3 | 53.3 | 70.3 | 28.4 | −5.0 | 28.8 |
| 10 | Blue | 134 | 350 | 67 | 58.3 | 0.1 | −54.1 | 54.1 | 68.0 | 30.5 | −7.0 | 31.3 |
| 11 | Blue | 134 | 365 | 50 | 56.9 | 0.4 | −52.5 | 52.5 | 66.2 | 30.2 | −6.9 | 31.0 |
| 12 | Turquoise | 134 | 329 | 129 | 72.5 | −30.6 | −31.0 | 43.6 | 68.4 | 37.1 | −18.1 | 41.3 |
| 13 | Turquoise | 134 | 350 | 95 | 71.2 | −34.3 | −33.5 | 47.9 | 65.6 | 40.8 | −23.6 | 47.1 |
| 14 | Turquoise | 134 | 365 | 76 | 69.5 | −35.9 | −34.4 | 49.7 | 63.2 | 44.1 | −27.1 | 51.8 |
| 15 | Turquoise | 134 | 380 | 60 | 67.1 | −34.7 | −34.8 | 49.1 | 61.1 | 45.7 | −28.5 | 53.9 |
| 16 | Green | 134 | 277 | 222 | 64.7 | −54.7 | 0.1 | 54.7 | 63.5 | 42.9 | −13.7 | 45.0 |
| 17 | Green | 134 | 292 | 210 | 69.4 | −53.3 | −0.4 | 53.3 | 63.1 | 43.2 | −18.6 | 47.0 |
| 18 | Green | 134 | 307 | 198 | 74.1 | −50.1 | 0.5 | 50.1 | 62.9 | 42.3 | −24.6 | 48.9 |
| 19 | Green | 134 | 329 | 179 | 79.7 | −43.3 | 2.2 | 43.4 | 63.0 | 37.9 | −32.4 | 49.9 |

[1] ±12 nm
[2] ±8 nm
[3] Normal incident hue. The hue of the interference color resulting from a viewing angle which is perpendicular to the plane of the drawdown card, and in which the incident light upon the drawdown card is also from the perpendicular or near it.

What is claimed is:

1. A multilayer effect pigment comprising:
a transparent substrate having a layer of titanium dioxide thereon, the optical thickness of said first layer of titanium dioxide being such as to provide a white hue to said substrate;
a layer of a low refractive index material on said titanium dioxide layer and an outermost layer of a high refractive index material placed on said low refractive index material layer;
said outermost layer comprising titanium dioxide having a optical thickness of from about 45 to 240 nm, said low refractive index material layer having an optical thickness of at least 150 nm to provide a variable pathlength for light dependent on the angle of incidence of light impinging thereon;
each layer differs in refractive index from any adjacent layer by at least about 0.2 and wherein at least one layer has an optical thickness which is different from all of the other layers, whereby the pigment is not a quarter-wave stack;
said multilayer effect pigment having a non-white hue, and wherein the pigment has a chromaticity of at least 40.0.

2. The multilayer effect pigment of claim 1 wherein said transparent substrate is glass flake.

3. The multilayer effect pigment of claim 1 in which the low refractive index material is silicon dioxide.

4. The multilayer effect pigment of claim 3 in which the optical thickness of said inner layer of titanium dioxide is about 134±12 nm.

5. The multilayer effect pigment of claim 4 wherein the optical thickness of said silicon dioxide layer is 219±8 nm and said outermost layer has an optical thickness of 95±12 nm and said pigment has a normal gold hue.

6. The multilayer effect pigment of claim 4 wherein the optical thickness of said silicon dioxide layer is 263±8 nm and said outermost layer has an optical thickness of 48±12 nm and said pigment has a normal gold hue.

7. The multilayer effect pigment of claim 4 wherein the optical thickness of said silicon dioxide layer is 219±8 nm and said outermost layer has an optical thickness of 177±12 nm and said pigment has a normal red hue.

8. The multilayer effect pigment of claim 4 wherein the optical thickness of said silicon dioxide layer is 467±8 nm and said outermost layer has an optical thickness of 215±12 nm and said pigment has a normal red hue.

9. The multilayer effect pigment of claim 4 wherein the optical thickness of said silicon dioxide layer is 292±8 nm and said outermost layer has an optical thickness of 95±12 nm and said pigment has a normal violet hue.

10. The multilayer effect pigment of claim 4 wherein the optical thickness of said silicon dioxide layer is 307 to 329±8 nm and said outermost layer has an optical thickness of 48±12 nm or 72±12 nm and said pigment has a normal violet hue.

11. The multilayer effect pigment of claim 4 wherein the optical thickness of said silicon dioxide layer is 329 to 336±8 nm and said outermost layer has an optical thickness of 84±12 nm or 95±12 nm and said pigment has a normal blue hue.

12. The multilayer effect pigment of claim 4 wherein the optical thickness of said silicon dioxide layer is 350 to 365±8 nm and said outermost layer has an optical thickness of 50±12 nm or 67±12 nm and said pigment has a normal blue hue.

13. The multilayer effect pigment of claim 4 wherein the optical thickness of said silicon dioxide layer is 329±8 nm and said outermost layer has an optical thickness of 129±12 nm and said pigment has a normal turquoise hue.

14. The multilayer effect pigment of claim 4 wherein the optical thickness of said silicon dioxide layer is 350 to 365±8 nm and said outermost layer has an optical thickness of 16±12 nm or 95±12 nm and said pigment has a normal turquoise hue.

15. The multilayer effect pigment of claim 4 wherein the optical thickness of said silicon dioxide layer is 380±8 nm and said outermost layer has an optical thickness of 60±12 nm and said pigment has a normal turquoise hue.

16. The multilayer effect pigment of claim 4 wherein the optical thickness of said silicon dioxide layer is 277 to 307±8 nm and said outermost layer has an optical thickness of 198 to 210±12 nm and said pigment has a normal green hue.

17. The multilayer effect pigment of claim 4 wherein the optical thickness of said silicon dioxide layer is 329±8 nm and said outermost layer has an optical thickness of 179±12 nm and said pigment has a normal green hue.

18. In a paint or ink composition including a pigment, the improvement which comprises said pigment being the effect pigment of claim 1.

19. In a plastic composition including a pigment, the improvement Which comprises said pigment being the effect pigment of claim 1.

20. In a cosmetic composition including a pigment, the improvement which comprises said pigment being the effect pigment of claim 1.

21. The multilayer effect pigment of claim 1 wherein the pigment has a chromaticity of at least 50.0.

* * * * *